United States Patent [19]
Smit et al.

[11] Patent Number: 5,245,065
[45] Date of Patent: Sep. 14, 1993

[54] PROCESS FOR THE PREPARATION OF DI-ALKYL COMPOUNDS OF GROUP 2B METALS

[75] Inventors: Cornelis J. Smit; Gerardus P. M. Van Mier; Henricus P. B. Duijghuisen, all of Arnhem, Netherlands

[73] Assignee: Shell Research Limited, London, United Kingdom

[21] Appl. No.: 971,876

[22] Filed: Nov. 5, 1992

[30] Foreign Application Priority Data

Nov. 19, 1991 [EP] European Pat. Off. ............ 91203015

[51] Int. Cl.$^5$ ............................ C07F 3/06; C07F 3/08; C07F 3/00
[52] U.S. Cl. ..................................................... 556/129
[58] Field of Search ........................................... 556/129

[56] References Cited

U.S. PATENT DOCUMENTS

| | | | |
|---|---|---|---|
| 3,087,947 | 4/1963 | Foster et al. | 260/429 |
| 3,475,475 | 10/1969 | Eidt | 260/429.9 |
| 4,812,586 | 3/1989 | Mullin et al. | 556/129 |
| 4,841,082 | 6/1989 | Eidt et al. | 556/129 |

Primary Examiner—Jose G. Dees
Assistant Examiner—Porfirio Nazario

[57] ABSTRACT

Di-alkyl compounds of a Group 2b metal is reacted with an alkyl halide in the presence of magnesium to obtain the di-alkyl compound of the Group 2b metal and magnesium halide. Di-alkyl compound-containing products are obtainable from the resulting product mixture having a halogen content of less than 1 ppm, a silicon content of less than 1 ppm and a Group 3a metal content of less than 1 ppm.

10 Claims, No Drawings

PROCESS FOR THE PREPARATION OF DI-ALKYL COMPOUNDS OF GROUP 2B METALS

FIELD OF THE INVENTION

The present invention relates to a process for the preparation of di-alkyl compounds of Group 2b metals, and to such compounds of specified purity. In this specification by "Group 2b metals" is meant zinc, cadmium and mercury.

BACKGROUND OF THE INVENTION

Di-alkyl compounds of Group 2b metals find increasing use in the electronics industry. Compounds and alloys containing elements such as zinc and cadmium are deposited on substrates from volatile precursor compounds, such as their respective di-alkyl compounds, by thermal decomposition from the vapor phase to give a thin (semiconductor) layer. This technique is known in the industry as Metal Organic Chemical Vapor Deposition (MOCVD). When an epitaxial layer is grown the technique is better known as Metal Organic Vapor Phase Epitaxy (MOVPE). A process for the deposition of zinc sulfide films on a semiconductor substrate in which di-alkyl zinc is used in combination with hydrogen sulfide is described in European patent application No. 405,875. A method for the preparation of epitaxial layers of zinc sulfide and zinc selenide is described in U.K. patent application No. 2,221,924.

The presence of impurities in such semiconductor layers has a substantial adverse effect on both their electrical and their optical properties. It is desired that the precursor compounds, such as the di-alkyl compounds of the Group 2b metals, are very pure. For the production of p-type zinc selenide layers for use in opto-electronic devices, the iodine content in the zinc precursor is of the utmost importance. Iodine is an n-type dopant and hence, controlled p-type doping can only be achieved if the iodine content in the epitaxial layer, and therefore in the zinc and selenium precursors, is very low, preferably below 1 ppm (by weight). Hence, it is not surprising that efforts have been made to purify these precursors, and particularly the di-alkyl compounds.

In U.S. patent specification No. 4,812,586 the purification of impure dimethylcadmium and dimethylzinc is described. According to this specification impure di-alkyl compounds are prepared by reacting methyl halide with magnesium to yield a Grignard reagent. This reagent is subsequently reacted with cadmium halide or zinc halide to yield the respective impure di-alkyl metal compound. This compound is purified by adduct formation with specific amino compounds followed by removal of impurities from the adduct. The purified adduct is subsequently dissociated and subjected to distillation to yield the purified di-alkyl compound. This process requires several steps.

In U.K. patent specification No. 1,242,789 a process is described in which metallic zinc is alkylated using alkyl halides in the presence of other metals, i.e., alkali metals. According to the examples of this specification the yields obtained in these examples range from 53% to 85%. However, it is apparent that in the example giving the highest yield, 0.220 mole zinc yielded 5.8 g or 47 mmole diethylzinc. Hence, the yield based on total zinc consumption was only 21%. This process requires an excess of zinc in addition to that which is contained in the di-alkyl compound, because zinc is used as halogen acceptor. If the use of very pure zinc is required, as would be the case for MOCVD or MOVPE purposes, this process would involve the waste of considerable amounts of pure zinc.

SUMMARY OF THE INVENTION

The present process relates to an improved preparation of di-alkyl metal compounds with an efficient use of the Group 2b metal. It has been found that the use of magnesium in the present process results in excellent yields and also in high purities. The invention further provides di-alkyl Group 2b metal compounds of specified high purity.

The present process therefore provides a process for the preparation of di-alkyl compounds of a Group 2b metal, comprising reacting a Group 2b metal with an alkyl halide in the presence of magnesium to obtain the di-alkyl compound of the Group 2b metal and magnesium halide.

DESCRIPTION OF THE INVENTION

The metals that are used in the process of the present invention are zinc, cadmium and mercury. Preferably, zinc or cadmium is used. In the most preferred embodiments, zinc is used.

The halogen moiety of the alkyl halide is selected from chlorine, bromine or iodine. Use of alkyl bromides and alkyl iodides are advantageous in the present process. Use of alkyl iodides tends to result in a product with the highest purity so their use is especially preferred.

The alkyl group in the alkyl halide compounds is straight-chain or branched. Although the present process can be carried out with a wide variety of alkyl halides, including those having long chain alkyl groups, the preparation of di-alkyl Group 2b metal compounds containing alkyl groups with up to 6 carbon atoms inclusive is preferred. The alkyl group in the alkyl halide more preferably has from 1 to 4 carbon atoms inclusive, e.g., methyl, ethyl, propyl, isopropyl or butyl. Most preferably, the alkyl moiety is methyl or ethyl or mixtures thereof.

The reaction is carried out under mild reaction conditions. The pressure is suitably atmospheric, but subatmospheric or super-atmospheric pressures are also useful. The pressure is typically from 0.1 bar to 10 bar. Largely for reasons of convenience it is preferred to carry out the process at atmospheric pressure. The di-alkyl compound is prepared under an inert atmosphere, e.g., nitrogen, argon or helium. The reaction temperature is selected so that the reaction temperature does not exceed the decomposition temperature of the di-alkyl compound involved. Such decomposition temperature is different for each di-alkyl compound but the process is suitably carried out at a temperature from about 20° C. to about 170° C. The process is suitably carried out in the presence of a solvent. The solvent ensures a homogenous distribution of the reactants and also provides a convenient means for controlling the dissipation of the heat evolved in the exothermic reaction. A wide variety of solvents are used in the present process. Such solvents include aliphatic or aromatic hydrocarbons, such as pentane, hexane, heptane, benzene, toluene or xylene, amides such as N,N-dimethylacetamide and dimethylformamide, and ethers, e.g., a cyclic ether such as tetrahydrofuran or dioxane, or a non-cyclic ether, such as diethyl ether, di-(iso)propyl ether, diphenyl ether, diglyme, triglyme and tetraglyme. Preferably, the solvent is an ether of at least 8 carbon atoms with a relatively high boiling point. Such ethers include diphenyl ether and in particular di-isopentyl ether.

Although it is possible to use a minor amount of magnesium in the present process, it is advantageous to use a substantially stoichiometric molar ratio of magnesium with respect to the Group 2b metal. The amount of magnesium preferably ranges from about 0.8 equivalent to about 2.0 equivalent magnesium per equivalent of Group 2b metal. The purity of the product obtained is enhanced if a relatively small excess of magnesium is employed. Therefore, the amount of magnesium is more preferably from about 1.0 equivalent to about 1.15 equivalent magnesium per equivalent Group 2b metal. The form in which the Group 2b metal and magnesium are present in the reaction mixture is not critical. It is possible to use a physical mixture of magnesium and the Group 2b metal involved. It is also feasible to employ an alloy of the metals. The relative amounts of metals in the alloy or the mixture suitably correspond to the above molar ratios.

In the present process, at least a substantially stoichiometric amount of alkyl halide is used. The yields of the desired di-alkyl compound are enhanced if an excess of alkyl halide is used, but in such cases the amount of unreacted reactant or by-products may contaminate the desired di-alkyl compound. Hence, it is useful to conduct the process at a molar ratio of alkyl halide to Group 2b metal of about 0.8:1 to about 4:1. However, if purity is paramount, the process is preferably carried out at substantially stoichiometric ratios. Therefore, the molar amount of alkyl halide is preferably substantially twice that of the Group 2b metal.

After completion of the reaction, the reaction mixture will contain the di-alkyl compound of the group 2b metal, magnesium halide, and the solvent employed. When an excess of magnesium is used, the reaction mixture will also contain unreacted magnesium. The di-alkyl compound is isolated from the reaction mixture by conventional techniques, including filtration and decantation. Preferably, the di-alkyl compound is recovered by distillation. After a first distillation, a second fractional distillation is often employed. In the isolation of the di-alkyl compound of the Group 2b metal from the reaction mixture by distillation it is typically advantageous to recover the first 1 percent to 10 percent by volume of the di-alkyl compound product separately. The main fraction of the desired product which is subsequently recovered has an enhanced purity. The first fraction of the distilled product is usefully recycled by adding it to the original reaction mixture or to a subsequent batch of reaction mixture, or is discarded. In order to avoid any possible thermal decomposition of the di-alkyl compound, distillation is advantageously carried out a temperature below the decomposition temperature of the di-alkyl compound involved. For certain di-alkyl compounds it is useful to perform the distillation under subatmospheric pressure, e.g., from below about 1 bar to as low as less than about 1 mbar.

The present invention produces di-alkyl compound of a Group 2b metal with excellent purity. The present invention provides a product containing at least 99.999% wt of a di-alkyl compound of a Group 2b metal and les than 1 ppm (parts per million by weight) halogen, less than 1 ppm silicon and less than 1 ppm of a Group 3a metal. The silicon content in the di-alkyl compounds suitably ranges from 0.01 to 1 ppm. Group 3a metals, e.g., gallium, aluminum or indium, are substantially absent, but suitably are present in an amount less than 0.5 ppm.

In the prior art processes which employ at least one halogen-containing reactant compound, the Group 2b metal compound or the alkyl compound, the residual content of halogen is up to about 1000 ppm. However, for the application of the di-alkyl Group 2b compound in Metal Organic Chemical Vapor Deposition or Metal Organic Vapor Phase Epitaxy of layers for the electronics industry, the purity of the di-alkyl compound is of the utmost importance, particularly with respect to such halogen species. Therefore, the provision of compounds with the purity as obtained in the present invention is extremely advantageous in this industry. A purity of from about 0.05 to 0.5 ppm halogen is obtainable by the process of the invention and the invention also related to such substantially pure products comprising di-alkyl compounds with less than 1 ppm of halogen, particularly products with from about 0.05 ppm to about 0.5 ppm halogen. The halogen most frequently used is iodine, particularly with zinc. The most preferred compounds are dimethylzinc and diethylzinc containing less than 1 ppm halogen.

Since the compounds according to the present invention are very suitable for use in MOCVD or MOVPE applications, the compounds of the present invention are particularly useful in MOCVD or MOVPE.

The invention is further illustrated by means of the following examples. In the examples the silicon content was determined by ICP-OES (inductively coupled plasma-optical emission spectroscopy), using tetramethyl silane as standard, and the iodine content was determined by ICP-MS (inductively coupled plasma-mass spectrometry), using methyl or ethyl iodine as standard.

EXAMPLE 1

Preparation of dimethylzinc

To a suspension of 73.74 g (1.128 mole) of zinc and 28.80 g (1.184 mole) of magnesium in 480 ml of di-isopentyl ether was added 320 g (2.256 mole) of methyl iodine at such a rate that the temperature rose to 110° C. After completion of the methyl iodide addition, the reaction was allowed to go to completion under agitation at 70° C. Subsequently, the reaction mixture was cooled to 40° C. and any unreacted methyl iodide was removed in vacuo. The reaction mixture was then heated to about 99° C. and distillation of dimethylzinc begun. As the distillation proceeded, the temperature was increased to about 170° C. During the distillation, a forerun of about 10% of the expected yield was taken. Thereafter the main fraction was obtained, which represented a yield of dimethylzinc of about 73%, based on zinc. The purity of the main fraction is illustrated by the silicon content (<0.3 ppm), determined by ICP-OES, and lead content (<0.2 ppm), determined by ICP-MS. The iodine content was 0.4 ppm as determined by ICP-MS, using methyl iodide as standard.

EXAMPLE 2

Preparation of diethylzinc

By a process substantially similar to that of Example 1, diethylzinc was prepared from zinc (1.056 mole), magnesium (1.111 mole) and ethyl iodide (2.112 mole) in 450 ml of di-isopentyl ether. The reaction temperature was maintained at a temperature below 100° C. to avoid decomposition of diethylzinc. The distillation was carried out at a decreasing pressure of 100 mbar to 16 mbar. The bottoms temperature did not exceed 98° C. The first few percent of distilled diethylzinc were discarded and the main fraction was recovered as product. The yield of recovered diethylzinc was about 86% based on zinc. The silicon content was <0.9 ppm. No other impurities were detected by ICP-OES. Further purification by distillation was accomplished to yield a diethylzinc fraction with a silicon content <0.1 ppm and a iodine content of <0.5 ppm, as determined by ICP-MS, using ethyl iodide as standard.

EXAMPLE 3

Preparation of dimethylcadmium

A series of experiments was carried out in which dimethylcadmium was prepared from cadmium, magnesium, methyl iodide in di-isopentyl ether. The procedure was similar to one described for the dimethylzinc preparation. The relative amounts of the reactants and the yields obtained are indicated in the table below.

TABLE

| Experiment | Molar Equivalents of Reactants | | | Yield DMC |
|---|---|---|---|---|
| No. | Cd | Mg | Methyl Iodide | % on Cd |
| 3.1 | 1.0 | 1.11 | 2.24 | 64 |
| 3.2 | 1.0 | 1.05 | 2.04 | 30 |
| 3.3 | 1.0 | 1.11 | 2.23 | 69 |
| 3.4 | 1.0 | 1.11 | 2.64 | 42 |

What is claimed:

1. A process for the preparation of di-alkyl compounds of a Group 2b metal by reacting a Group 2b metal with an alkyl halide in the presence of magnesium to obtain the di-alkyl compound of the Group 2b metal and magnesium halide and recovering the di-alkyl Group 2b metal compound from the resulting mixture.

2. The process of claim 1 in which the Group 2b metal is zinc or cadmium.

3. The process of claim 2 in which the alkyl halide is an alkyl iodide.

4. The process according to claim 3 carried out at a temperature from about 20° C. to about 170° C.

5. The process of claim 4 carried out in the presence of a solvent.

6. The process of claim 3 in which the amount of magnesium is from about 0.80 equivalents to about 2.0 equivalents of magnesium per equivalent of Group 2b metal.

7. The process of claim 6 in which the molar ratio of the Group 2b metal to the alkyl halide is from about 0.8:1 to about 4:1.

8. The process of claim 7 wherein the molar ratio is substantially stoichiometric.

9. Product containing at least 99.999% wt of a di-alkyl compound of a Group 2b metal and less than 1 ppm halogen, less than 1 ppm of a Group 3a metal and less than 1 ppm silicon.

10. Product according to claim 9 which contains from 0.05 ppm to 0.5 ppm halogen.

* * * * *